United States Patent
Da Silva

(10) Patent No.: US 11,650,189 B2
(45) Date of Patent: May 16, 2023

(54) GRAIN SEPARATION AUTOMATION AND PROCESSING EQUIPMENT AND POSSIBLE MATERIALS OF IDENTIFICATION, CLASSIFICATION AND QUANTIFICATION OF THE SAME; APPLICATION OF PROCESS AND USE OF EQUIPMENT

(71) Applicant: Manoel Henrique Da Silva, Curitiba (BR)

(72) Inventor: Manoel Henrique Da Silva, Curitiba (BR)

(*) Notice: Subject to any disclaimer, the term of this patent is extended or adjusted under 35 U.S.C. 154(b) by 367 days.

(21) Appl. No.: 16/794,329

(22) Filed: Feb. 19, 2020

(65) Prior Publication Data

US 2021/0048421 A1    Feb. 18, 2021

(30) Foreign Application Priority Data

Aug. 15, 2019  (BR) ............... 10 2019 016975 3

(51) Int. Cl.
*G01N 33/02*    (2006.01)
*B07C 5/342*    (2006.01)
(Continued)

(52) U.S. Cl.
CPC ......... *G01N 33/025* (2013.01); *B07C 5/3425* (2013.01); *B07C 5/36* (2013.01);
(Continued)

(58) Field of Classification Search
CPC ...... G01N 33/025; B07C 5/3425; B07C 5/36; B65B 1/04; B65B 1/32; B65B 57/10;
(Continued)

(56) References Cited

U.S. PATENT DOCUMENTS 4,718,558 A * 1/1988 Castaneda ............. B07C 5/3425
                                                              209/546
5,245,188 A * 9/1993 Satake ................. B07C 5/3425
                                                              250/341.7
(Continued)

FOREIGN PATENT DOCUMENTS

CN     105363691 A  *  3/2016
CN     106423880 A  *  2/2017  ........... B07B 13/003
(Continued)

*Primary Examiner* — Gene O Crawford
*Assistant Examiner* — Muhammad Awais
(74) *Attorney, Agent, or Firm* — Bay State IP, LLC

(57) ABSTRACT

The present application is related to the process of automation of separation by identification, classification and quantification of grains and their possible pertinent materials through equipment that performs such events, aiming at the automation of the whole chain of separation, identification and classification. grain, thus eliminating the human action of the process and thus avoiding errors related to human interaction in the process. This process has 4 steps, as follows: grain and impurities entering the equipment; separation of impurities and grains: grain processing and qualitative and quantitative identification of grains and impurities. The process and equipment can be applied to the separation by identification, classification and quantification of grains such as soybeans, corn, among others, and their possible pertinent materials.

6 Claims, 5 Drawing Sheets

(51) Int. Cl.
*B07C 5/36* (2006.01)
*B65B 57/10* (2006.01)
*B65B 1/32* (2006.01)
*B65B 1/04* (2006.01)
*B03B 4/06* (2006.01)
*B03B 9/00* (2006.01)
*B03B 13/00* (2006.01)

(52) U.S. Cl.
CPC ............... *B65B 1/04* (2013.01); *B65B 1/32* (2013.01); *B65B 57/10* (2013.01); *B03B 4/06* (2013.01); *B03B 9/00* (2013.01); *B03B 13/00* (2013.01)

(58) Field of Classification Search
CPC ... B03B 4/06; B03B 9/00; B03B 13/00; A01F 12/42; A01F 12/44; A01F 12/50; A01F 12/442; B07B 4/00; B07B 4/02; B07B 4/06; B07B 4/08
USPC .......................................... 209/233
See application file for complete search history.

(56) References Cited

U.S. PATENT DOCUMENTS

| | | | | |
|---|---|---|---|---|
| 5,713,473 A | * | 2/1998 | Satake | B07C 5/3416 198/813 |
| 5,865,990 A | * | 2/1999 | Novak | B07C 5/3416 209/579 |
| 5,956,413 A | * | 9/1999 | Oste | B07C 5/3425 382/110 |
| 5,994,656 A | * | 11/1999 | Satake | B07C 5/365 209/580 |
| 2019/0141909 A1 | * | 5/2019 | Klooster | A01G 9/085 111/200 |

FOREIGN PATENT DOCUMENTS

| | | | | |
|---|---|---|---|---|
| CN | 109530267 A | * | 3/2019 | ............ B07B 9/00 |
| DE | 202011108744 U1 | * | 3/2012 | ............ B07B 4/08 |
| KR | 20080004954 A | * | 1/2008 | |
| WO | 2017/042760 A1 | | 3/2017 | |
| WO | WO-2017042760 A1 | * | 3/2017 | |
| WO | WO-2019022690 A1 | * | 1/2019 | |

* cited by examiner

GRAIN SEPARATION AUTOMATION AND PROCESSING EQUIPMENT AND POSSIBLE MATERIALS OF IDENTIFICATION, CLASSIFICATION AND QUANTIFICATION OF THE SAME; APPLICATION OF PROCESS AND USE OF EQUIPMENT

CROSS REFERENCE TO RELATED APPLICATION

This application takes priority from and claims the benefit of Brazilian Patent Application No. 102019016975-3 filed on Aug. 15, 2019, the contents of which are herein incorporated by reference.

BACKGROUND OF THE INVENTION

The present patent application is related to the process of automation of separation by identification, classification and quantification of grains and their possible materials pertinent to the process, by means of equipment that performs such events, aiming at the automation of the whole chain, separation by identification and classification of grains, thus eliminating the human action of the process and thus avoiding errors related to human interaction in the process. It also refers to the application of the process and the use of equipment, both in the stages of separation by identification, classification and quantification of grains and their possible materials relevant to the process.

FIELD OF THE INVENTION

This patent application relates to the field of agriculture.

DESCRIPTION OF THE RELATED ART

According to the Ministry of Agriculture, Brazil's crop forecast for 2018/2019 will be 238 million tons, which represents 23% of all Brazilian GDP. The end of the cycle of all this production is the classification of grains, carried out at the time of commercialization, with the final destination being processing, exporting to other countries and producing food.

The process of classification of grain is currently governed by the Legislation of MAPA (Ministry of Agriculture, Livestock and Supply), following the Normative Instruction No. 11, May 15, 2007, which governs the Official Classification of SOYA. This instruction describes rules and procedures that must be followed for a standardization of the grain classification process, which aims, through this procedure, to reduce errors and increase the quality of the process. But this process still depends on human action, which is susceptible to errors, either on purpose or inattention during the process.

Currently some equipment performs some of these operations.

However, these devices perform only part of the process: some only identify grains with computational vision; others separate but do not weigh at the end of the process.

U.S. Pat. No. 5,865,990 describes a rice sorter using a method of spreading grain by centripetal force. With scattered grains, a laser system identifies the good and bad grains. This model only contemplates the identification part, and uses a method that does not allow the grain to be viewed 360°.

U.S. Pat. No. 5,956,413 describes an automatic grain evaluation system which is conveyed by a conveyor belt with a vibration system which spreads the grain along that belt. With grains properly scattered and with the same orientation, a vision system makes images of all grains, and classifies them using an Artificial Neural Network. In this model, a conveyor belt is used to accommodate the grain, where the system only generates images of the top of the grain, not allowing a more detailed analysis of it.

European Patent WO 2017/042760 describes a grain sorting system comprising a mobile robotic structure capable of performing the grain detection, selection and sorting processes that are on a conveyor belt. In particular, this system is designed to classify husked coffee beans. More particularly, this system comprises four video cameras that capture images of the grain conveyor belt. These video images are sent to a control unit that processes them and obtains information about color, size and shape. Thus, when the grain does not meet quality standards based on color, size and shape, it is selected and removed from the conveyor belt, leaving only the grain that meets these standards. In this model the analyzed images also only comprise the upper part of the grains, not allowing a more complete analysis. As for the separation system, the samples are placed in containers, but are not weighed, not allowing to measure the percentage of separated grains with anomalies of the rest of the sample.

SUMMARY OF THE INVENTION

Although the object of the invention is to automate a process that is now 100% manual, its use will not dispense with the use of human labor; The professional who today performs this function, called GRAIN GRADER, performs the classification as follows: Each grain type has a specific Legislation officially published through Normative Instructions by the MAPA (Ministry of Agriculture, Livestock and Supply) based on international grain classification and quality control practices. One process is to separate and quantify how much impurity, foreign matter, and imperfect grain is in a batch of grain, because at the time of marketing, each type of impurity or imperfect grain has a tolerance accepted by the buyer, which exceeds this tolerance, discounted proportionally. The CLASSIFIER then separates on average 125 grs of the pre-homogenized sample received, passes through a specific sieve screen for removal of impurities and foreign matter, then takes the sample to a generally blue-bottomed table with focused light focus to give greater contrast to the grains you are analyzing. It then visually analyzes grain by grain and within its knowledge separates into different types of defects in containers. For each type of grain there is a list of defects and for each defect there are percentages of involvement that interferes with the grain. For example, a grain may be 20% or 50% or 80% burned. After separation, the quantities of all containers are weighed on a scale and their weight is calculated on a calculator to find out how much each type of defect represents in relation to the weight of the sample analyzed. This result found in the calculator is transcribed in the novel or typed in the buyer's system. It can be seen from this that the possibilities of errors or interpretation may vary dramatically when subjected to the same sample to different RATEERS. What is intended with the invention is not the replacement of the GRAIN GRADER by the invention. On the contrary, this professional trained in how to use the machine, should operate it by making the correct sample feed, set up the machine and through their knowledge, attest and audit the results offered by the machine.

DETAILED DESCRIPTION OF THE SEVERAL EMBODIMENTS

Figure 1A:
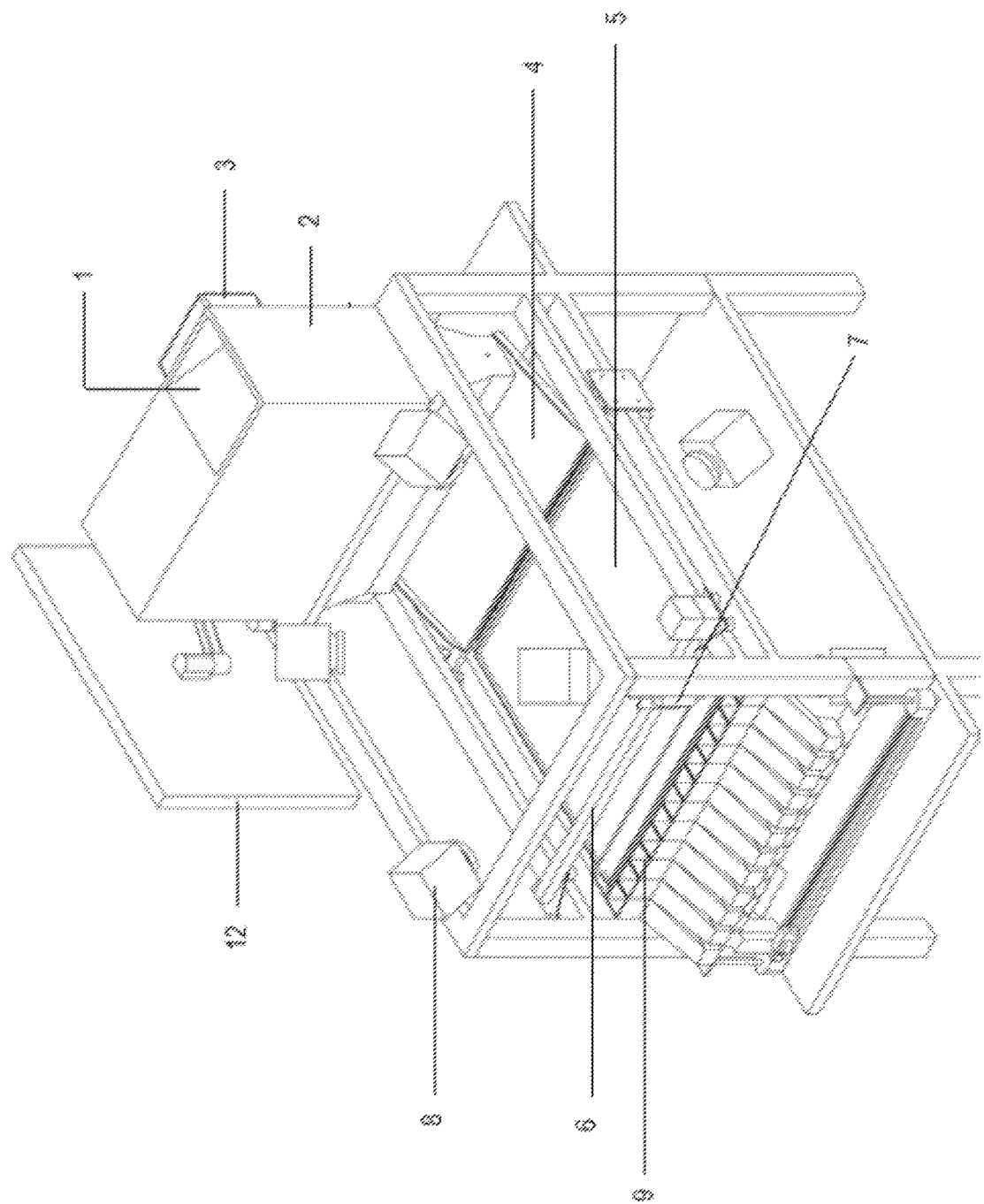
FIGS. 1A-1B illustrate a frontal view of the grain separation, identification, classification and quantification optimization equipment.
Figure 1B:
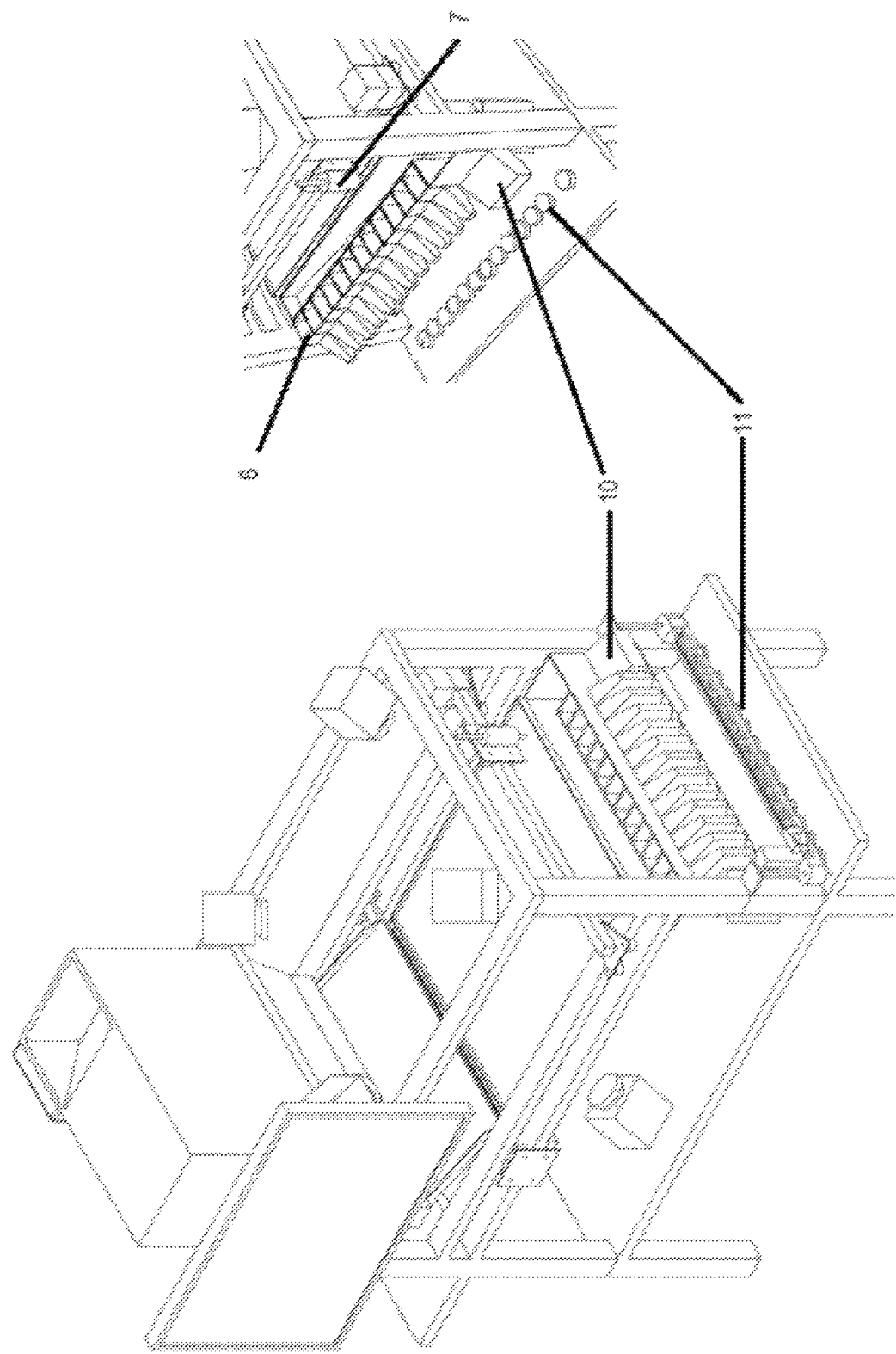

The present patent application contemplates the process of automation of separation by identification, classification and quantification of 10 types of grains (soy, maize, wheat, rice, beans, barley, oats, rye, sorghum and coffee) and of its possible materials pertinent to the process, by means of equipment that performs such events, aiming at the automation of the whole chain of separation by identification and classification of the grains, thus eliminating the human action of the process and thus avoiding errors related to human interaction in this process. The goal is to automate the entire process, allowing a density analysis to identify and determine product quality by weight. The proposal is to identify, classify, separate and quantify the sample analyzed when:

1. group;
2. class;
3. impurities and foreign matter;
4. FAULTS, which may be:
burned;
blazing;
Moldy;
Mild defects:
fermented;
greenish;
sprouted;
damaged;
immature;
chochos;
wrinkled;
Parties
broken;
Wormy;
plaster casts;
Triguillo, among others The present patent application will be explained by the detailed description of the figures:

FIGS. 1A-1B presents the frontal view of the grain separation, identification, classification and quantification optimization equipment, where they stand out: in 1A: (1) conical rectangular funnel for grain placement with grain type recognition and weighing device Sample; (2) reservoir for grain placement; (3) thermal printer; (4) homogeneous grain distributor; (5) classification glass table; (6) sliding robot arm with broom and CNC; (7) grain collector; (8) cameras (total of 8); (9) defective grain compartment; in 1B: (10) perfect grain funnel; (11) funnel load cell compartment; (12) Color touchscreen LCD for setup and dashboard.

Figure 2A:
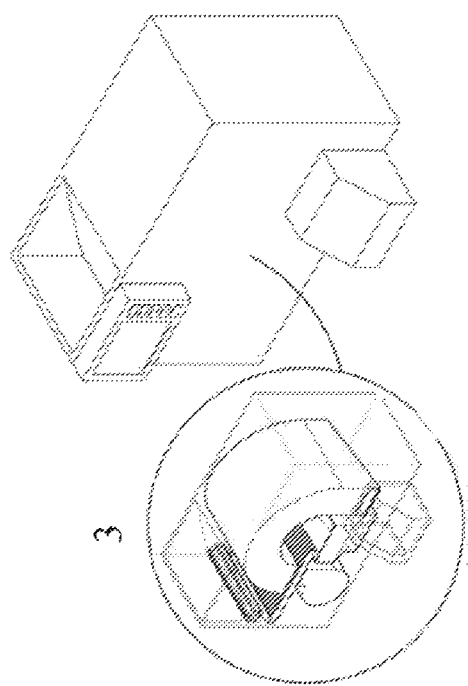
FIG. 2A illustrates a (3) thermal printer and a (12) Color touchscreen LCD for setup and dashboard.
Figure 2B:
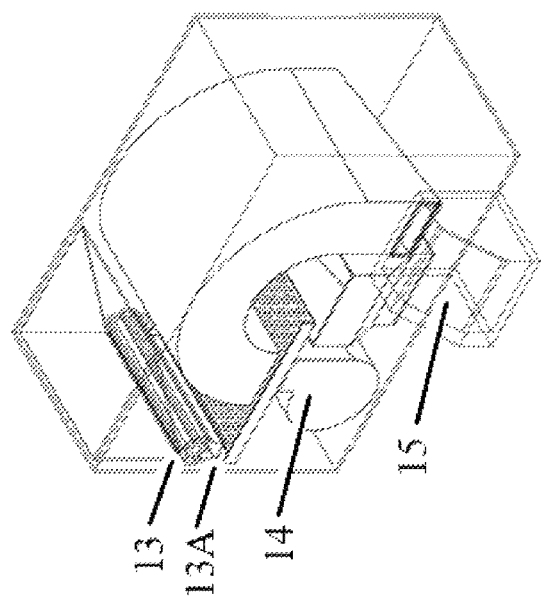
FIG. 2B illustrates an internal view of the grain separation, identification, classification and quantification system.
Figure 2C:
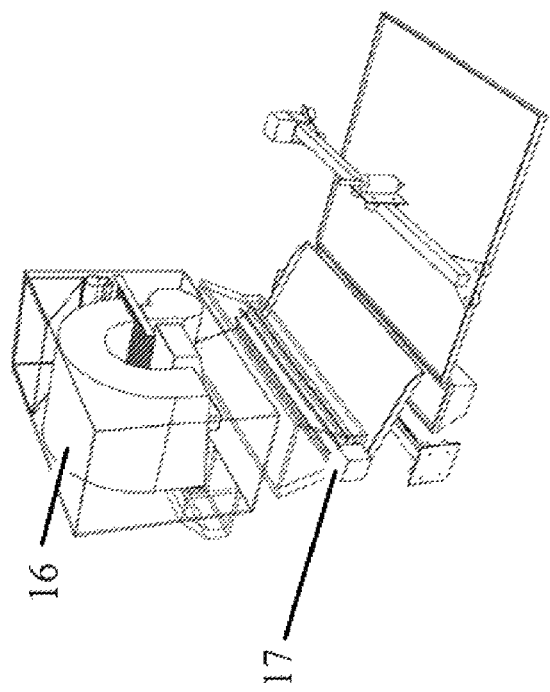
FIG. 2C illustrates a (16) lighter particle/impurity tunnel and (17) the rotary-spade sample dispenser.

FIGS. 2A-2C show as follows: in (2A): (3) thermal printer; (12) Color touchscreen LCD for setup and dashboard; in (2B), the internal view of the system, where: in (13a) the load cell for weighing the sample with the sample inlet closer; (13) presents the perforated platform with specific measures of each grain, respecting what governs the Official Standards, automatically selected according to the recognition of the type of grain to be analyzed; (14) blower; (15) reservoir of light impurities. In (2C), we present: (16) lighter particle/impurity tunnel; (17) the rotary-spade sample dispenser.

Figure 3:
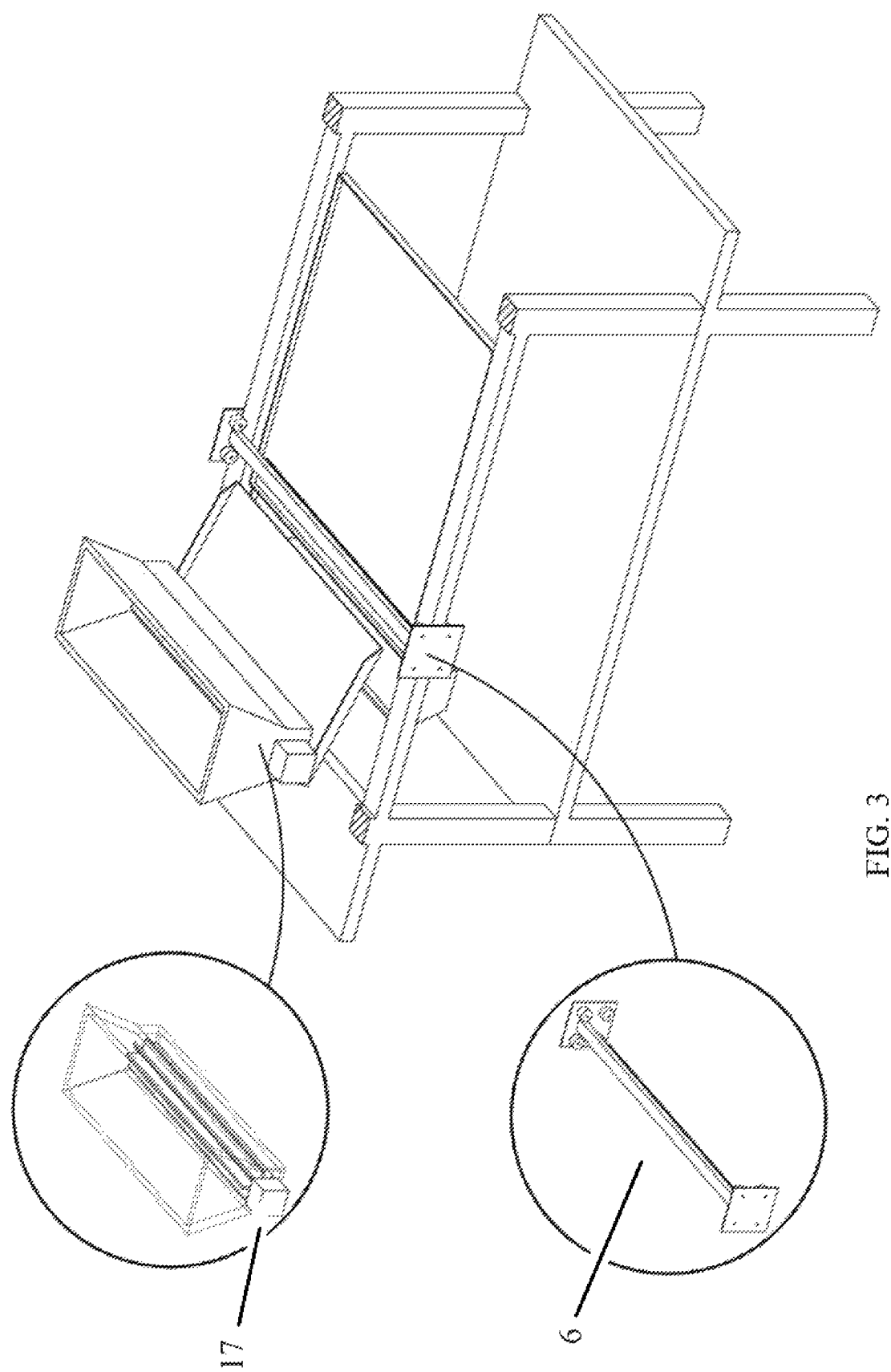
FIG. 3 illustrates an expanded view of the first grain dispenser.

FIG. 3 presents: in an expanded view of the first grain dispenser, where a rotating shovel (17) can be observed that distributes the grains evenly to the grading table; in (6) the sliding robot arm with broom and with CNC.

Figure 4:
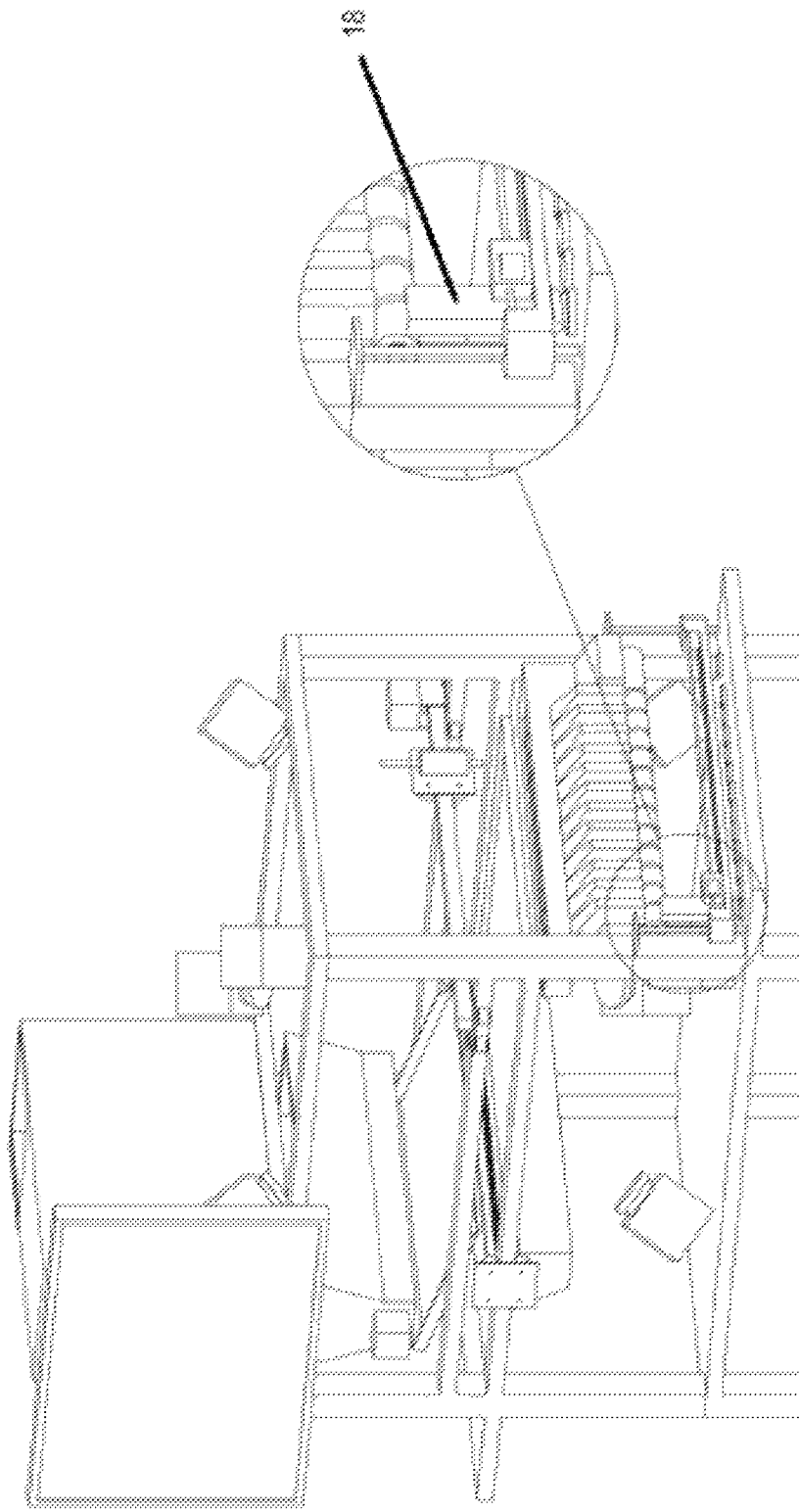
FIG. 4 illustrates an expanded view of the sealer (18).

FIG. 4 shows: an expanded view of the sealer (18).

The process of automating separation by identifying, grading and quantifying grains and their possible process-relevant materials by means of the equipment illustrated in FIGS. 1 to 3 is divided into 4 steps, explained below:

Step 1: Grain and Impurities Entry into the Equipment: Grains and impurities (up to 15 kg sample) are added to the tapered rectangular funnel (1) to quantify the initial amount of grains and impurities entering the system (initial material dosage). The grains and impurities, after being homogenized, are weighed and fall by rotary shovel control. This sample is weighed and becomes the reference weight. Automatic recognition (through imaging) of the type of grain to be analyzed is performed. The machine automatically configures the type of grain to be analyzed. After this procedure, the sample is automatically collected into the reservoir compartment.

Step 2: Separation of the impurities and grains: Said grains and impurities enter and lodge in the reservoir (3) which has a rotating blade (first closer) (17) which doses and distributes the grains and impurities evenly to the platform. perforated/screened (13). The perforated platform screen dimensions are already adjusted with the initial automatic setup performed in step 1, as well as the type of grain being analyzed, as each type of grain has a different dimension. When sliding on this platform, the sample suffers the action of a blower (14) that blows air to separate the lightest impurities (such as peels, leaves, among others) from the heavier ones (such as defective stones and grains, among others). The lighter impurities are directed by air to the lighter impurities/particles sending tunnel (16) to the reservoir for their collection (15). Lighter impurities are weighed and quantified against the reference weight, and then packaged, sealed and identified. The dispenser outlet opening can be adjusted for different sample types.

Step 3: Processing: The heaviest matter that has passed through the air curtain falls by gravity into a rectangular cone where it is dosed by a cylindrical rotating shovel into a narrow rectangular opening, generating a curtain of falling grain on a glass table. moving to a perfect distribution (5), in the shape of a rectangle. The table moves for a better distribution of the grains in all their extension and, with the help of the sliding CNC robot arm with broom (6) the grains are accommodated, avoiding overlapping of the same. To improve and ensure the correct spreading of the grains on the table, a horizontal rod of the same width as the table, equipped at its lower end with a bristle broom, passes horizontally over the grains, accommodating them on the table and avoiding overlapping of the grains. grains. After this step, the grains are detected by the cameras, positioned at 45° (8) and facing the table, which in turn make the reading and images in 360°, along with the aid of laser for depth identification.

Step 4: Qualitative and quantitative identification of grains and impurities: According to the initial automatic setup, the machine will program which types of defects it will analyze, as each type of grain has different analyzes, obtaining perfect grain recognition or any another particle, as well as its quantification. With the proper coordinates sent by the camera images, the robot arm identifies exactly the position of each grain. The table where the samples will be placed is made of glass/crystal (5), thus allowing images of both sides of the grains. Each camera in the system sends its images to a central, where they are processed to form only one image. The laser system is also triggered along with the cameras, identifying the depth in the images, a parameter that cannot be measured with digital images only. From these images after application of filters and algorithms of computer vision and artificial intelligence, we obtain, as a result, the classification of common types of malfunctions in samples. Once each grain is classified with the proper characteristics, the system identifies its location on the table in coordinate (X, Y) form. This coordinate is sent to the robotic system, consisting of a mechanical arm. At the end of the arm contains a suction cup system for individual collection of each grain placed on the table.

The robotic system consists of a 3-degree articulated arm, X, Y and Z, capable of manipulating small particles through a suction cup system, which will be coupled to its end. The control of the system is accomplished through a computer center, interconnected to the vision system. At one end, 20 containers are coupled for allocation of the different damaged grain types and or other types selected as per the standards specified above.

With the identified position, the robotic arm (7) collects the imperfect grains and impurities using a suction cup tip and distributes them to the impurity compartments (9) and the load cells (11) weigh it. the amount of impurities and imperfect grains, as well as identifying them by defect types. According to the classification made by the vision system, the arm collects the grains individually and places them in containers according to their classification (burnt, burnt, etc.). Each impurity compartment (9) is housed on a precision balance (load cell (11)), where the weight of each type of sample is identified, and sent to the system to calculate the percentage of said type of imperfection analyzed. After completion of the entire classification, each recipient that received the collected material individually presents its weighed, packaged, sealed (18), quantified and identified sample in relation to the initial reference sample. This identification contains: the type of grain, its classification, weight and percentage over the sample, with a QR Code that brings all the product information and analysis. The final result appears on screen (12) and can be printed on (3). If connected to a client computer, the results obtained are automatically transferred.

What is claimed is:

1. An automated method for grain separation and its possible materials of identification, classification and quantification, comprising the steps of:
    inputting of a quantity of grains and impurities in a grain separation equipment;
    adding of up to 15 kg of grains, grains and impurities to the conical rectangular funnel (1), with screen for the electronic setup (12);
    homogenizing and weighing of the grains and the impurities by a rotary blade control (17);
    separating of the impurities and grains;
    entering and housing of said grains and impurities in the reservoir (2) which has a rotating blade (first closer) (17);
    dosing of grains and impurities for the perforated/screened platform (13);
    air blasting (14) for separation of lighter impurities (such as bark, leaves, etc.) from heavier (such as defective stones and grains, among others);
    directing of the lighter impurities to the lighter impurities/particle sending tunnel (16) and to the reservoir (15) for the collection of lighter impurities/particles
    gravity triming of the heaviest sample in the rectangular cone;
    dosing of the sample by cylindrical rotating shovel into a narrow rectangular opening, generating a curtain of falling grain on a moving glass table for perfect distribution (5);
    table displacing, for better distribution of the grains in all its extension;
    even accommodating and spreading evenly of the grains with the aid of the CNC sliding robot arm and horizontal shank of the same width as the broom table (6);
    detecting grain by cameras positioned at 45° (8) and facing the table, which perform the reading and images in 360°, along with the aid of laser for depth identification;
    analyzing quantitatively each type of grain, according to the reading analyzed and the initial automatic setup performed by the machine;
    detecting and identification of the position of each grain type, by reading performed by the robotic system, with robotic arm and articulated with 3 degrees of movement, X, Y and Z;
    sending, by cameras, of each image made to the plant, and, with the aid of the laser, the depth of each grain is identified;
    assisting of computer vision algorithms to obtain the classification of the types of faults in the sample;
    collecting by the robotic arm (7) of the imperfect grains by suction cup system and distribution of the grains to the impurities compartments (9) and load cells (11) which weigh the amount of impurities and imperfect grains, as well as identify them by defect types;
    weighing a final sample is weighed, packaged, sealed (18), quantified and identified in relation to the initial reference sample, where the identification contains: the type of grain, its classification, weight and percentage over the sample with a code (QR) Code) which contains all product information and analysis; and
    wherein a final result appears on the screen (12) and can be printed and if connected to a client computer, the results obtained are automatically transferred.

2. The automated method for grain separation and its possible materials of identification, classification and quantification of claim 1, wherein the method is applied to the identification, classification and quantification of grains and their possible relevant materials.

3. The automated method for grain separation and its possible materials of identification, classification and quantification of claim 1, wherein the equipment is used for the automation of identification separation, classification and quantification of grains and their possible pertinent materials.

4. A grain separation automation equipment and its possible materials of identification, classification and quantification, wherein the equipment comprises:
- a (1) Conical rectangular hopper for grain placement;
- a (2) reservoir for grain placement;
- a (3) thermal printer;
- a (4) homogeneous grain distributor;
- a (5) classification glass table;
- a (6) sliding robot arm with broom and CNC;
- a (7) grain collector;
- a (8) cameras (total of 8);
- a (9) impurity compartment;
- a (10) clean grain funnel;
- a (11) funnel load cell compartment;
- a (12) Color touchscreen LCD for setup and dashboard;
- a (13a) the load cell for weighing the sample with the sample inlet closer;
- a (13) the perforated/screened platform;
- a (14) blower;
- a (15) reservoir of light impurities;
- a (16) lighter impurities/particle shipping tunnel;
- a (17) the rotary blade; and
- a sealer sample dispenser (18).

5. The automated method for grain separation and its possible materials of identification, classification and quantification of claim 4, wherein the method is applied to the identification, classification and quantification of grains and their possible relevant materials.

6. The automated method for grain separation and its possible materials of identification, classification and quantification of claim 4, wherein the equipment is used for the automation of identification separation, classification and quantification of grains and their possible pertinent materials.

* * * * *